United States Patent [19]

Lesher et al.

[11] Patent Number: 4,515,797

[45] Date of Patent: May 7, 1985

[54] 3-AMINO-5-(HYDROXY- AND/OR AMINOPHENYL)-6-(LOWER-ALKYL)-2(1H)-PYRIDINONES AND CARDIOTONIC USE THEREOF

[75] Inventors: George Y. Lesher; Chester J. Opalka, Jr., both of Schodack; Donald F. Page, East Greenbush, all of N.Y.

[73] Assignee: Sterling Drug Inc., New York, N.Y.

[21] Appl. No.: 355,229

[22] Filed: Mar. 5, 1982

Related U.S. Application Data

[63] Continuation-in-part of Ser. No. 300,294, Sep. 8, 1981, abandoned, which is a continuation-in-part of Ser. No. 348,450, Feb. 12, 1982, abandoned, which is a continuation-in-part of Ser. No. 248,840, Mar. 30, 1981, abandoned.

[51] Int. Cl.$^3$ .................... A61K 31/44; C07D 211/72
[52] U.S. Cl. .................... 514/349; 546/300; 546/301
[58] Field of Search ............... 546/300, 301; 424/263

[56] References Cited

U.S. PATENT DOCUMENTS

| | | |
|---|---|---|
| 3,655,679 | 4/1972 | Shen et al. |
| 3,703,582 | 11/1972 | Shen et al. |
| 3,718,743 | 2/1973 | Shen et al. |
| 3,853,896 | 12/1974 | Pessolano et al. ............ 546/300 |
| 4,004,012 | 1/1977 | Lesher et al. |
| 4,072,746 | 2/1978 | Lesher et al. |
| 4,297,362 | 10/1981 | Lesher et al. |
| 4,302,462 | 11/1981 | Collins et al. |
| 4,313,951 | 2/1982 | Lesher et al. |
| 4,377,585 | 3/1983 | Lesher et al. ............ 546/300 |
| 4,431,651 | 2/1984 | Lesher et al. ............ 546/301 |
| 4,465,686 | 8/1984 | Lesher et al. ............ 546/301 |

FOREIGN PATENT DOCUMENTS 2070606  9/1981  United Kingdom ............ 549/290

Primary Examiner—Ethel G. Love
Attorney, Agent, or Firm—Robert K. Bair; B. Woodrow Wyatt; Paul E. Dupont

[57] ABSTRACT

1-$R_1$-3-amino-5-(3-R'-4-R"-phenyl)-6-R-2(1H)-pyridinones or salts thereof, which are useful as cardiotonics, where $R_1$ is hydrogen, lower-alkyl, or lower-hydroxyalkyl, R is hydrogen or lower-alkyl, and, R' and R" are each hydrogen, hydroxy or amino at least one of R' or R" being other than hydrogen, are prepared by reacting the corresponding 3-carbamyl compound with a reagent capable of converting carbamyl to amino or by first reacting the corresponding 3-carbamyl compound where R' and R" are each hydrogen, nitro or lower-alkoxy at least one of R' and R" being other than hydrogen with a reagent capable of converting carbamyl to amino and then reacting the resulting 3-amino compound where R' and/or R" are/is lower-alkoxy and/or nitro with a reagent capable of converting lower-alkoxy to hydroxy and/or with a reagent capable of converting nitro to amino. Preparation of the corresponding 3-carbamyl and 3-cyano compounds is shown, the latter including cardiotonically active novel 1-$R_1$-1,2-dihydro-5-(3-$R_2$-4-$R_3$-phenyl)-6-R-nicotinonitriles where $R_1$ and R are defined as above, and $R_2$ and $R_3$ have the above given definitions for R' and R" or where $R_2$ is nitro and $R_3$ is hydroxy. Also shown are cardiotonic compositions and cardiotonic method of use of abovesaid compounds.

13 Claims, No Drawings

3-AMINO-5-(HYDROXY- AND/OR AMINOPHENYL)-6-(LOWER-ALKYL)-2(1H)-PYRIDINONES AND CARDIOTONIC USE THEREOF

CROSS-REFERENCE TO RELATED APPLICATIONS

This application is a continuation-in-part of copending applications Ser. No. 300,294, filed Sept. 8, 1981 and now abandoned, and Ser. No. 348,450, filed Feb. 12, 1982 now abandoned, which is a continuation-in-part of Ser. No. 248,840, filed Mar. 30, 1981 and now abandoned.

BACKGROUND OF THE INVENTION (a) Field of the Invention

This invention relates to 3-amino-5-(substituted-phenyl)-2(1H)-pyridinones, their preparation and use as cardiotonics, and to 1,2-dihydro-5-(substituted-phenyl)-2-oxo-nicotinonitriles, which are useful as cardiotonics and as intermediates in the preparation of said 3-amino-5-(substituted-phenyl)-2(1H)-pyridinones.

(b) Description of the Prior Art

Julia, et al., Bull. soc. chim. (France), 2387–2394 (1966), show inter alia the reaction of 1-hydroxymethylene-1-phenyl-2-propanone with α-cyanoacetamide to produce 2-hydroxy-5-(unsubstituted-phenyl)-6-methylnicotinonitrile and the reaction of 3-dimethylamino-2-phenyl-2-propenal (same as β-dimethylamino-α-phenylacrolein) with α-cyanoacetamide to produce 2-hydroxy-5-(unsubstituted-phenyl)nicotinonitrile. These 2-hydroxy compounds, tautomers of the corresponding 1,2-dihydro-2(1H)-pyridinones, were converted to their corresponding carboxylic acids and ethyl or methyl esters and also to their respective 2-chloro compounds and 5-(unsubstituted-phenyl)-3-piperidinecarboxamide derivatives, representative members of which were found to have pharmacological activity resembling that of lysergamide.

Shen et al [U.S. Pat. No. 3,718,743, issued Feb. 27, 1973] show "5-phenyl-2-piperidinones and 5-phenyl-2-thiopiperidinones in compositions and methods for treating pain, fever and inflammation". The generic teaching of these piperidinones shows that "phenyl" can have one or two substituents at positions 2, 3, 4, 5 and/or 6, e.g., inter alia, nitro, amino, lower-alkyl, lower-alkylamino and lower-alkylmercapto. Various means of preparing the 5-phenyl-2-piperidinone final products are shown. In one procedure, a 2-chloro-5-phenylpyridine was heated with aqueous sodium hydroxide in dimethylformamide to produce the corresponding 5-phenyl-2(1H)-pyridinones which were then hydrogenated to produce the desired 5-phenyl-2-piperidinones. Among the intermediate 5-phenyl-2(1H)-pyridinones specifically shown is 5-(4-hydroxyphenyl)-2(1H)-pyridinone as well as its preparation by heating the corresponding 5-(4-methoxyphenyl)-2(1H)-pyridinone with pyridine hydrochloride under nitrogen.

Shen et al [U.S. Pat. Nos. 3,655,679, issued Apr. 11, 1972, and 3,703,582, issued Nov. 21, 1972] show as anti-inflammatory, analgesic and antipyretic agents various aryl-hydroxy-pyridinecarboxylic acids and lower-alkyl esters thereof, among which are 5-(substituted-phenyl)-2-hydroxynicotinic acids; these latter compounds were prepared by reacting a 2-(substituted-phenyl)-3-dimethylamino-2-propenal with cyanoacetamide to first produce 5-(substituted-pheny)-2-hydroxynicotinonitrile, illustrated inter alia by the compounds where substituted-phenyl is 4-chlorophenyl, 3,4-dihydroxyphenyl, 4-nitrophenyl, 4-benzoylaminophenyl or 2,6-dimethoxyphenyl. Also shown is the preparation of the corresponding 2-hydroxy-6-methyl-5-(substituted-phenyl)-nicotinonitrile by reacting 2-(substituted-phenyl)-acetoacetaldehyde with cyanoacetamide followed by hydrolysis of the nicotinonitrile to the corresponding nicotinic acid; illustrations of intermediate nicotinonitriles produced by this procedure include inter alia the compounds where substituted-phenyl is 2-hydroxyphenyl, 4-methoxyphenyl or 4-aminophenyl.

Lesher and Opalka [U.S. Pat. Nos. 4,004,012, issued Jan. 18, 1977, and 4,072,746, issued Feb. 7, 1978] show as cardiotonic agents 3-amino(or cyano)-5-(pyridinyl)-2(1H)-pyridinones and as intermediates, the corresponding 3-carbamyl compounds, alternatively named 1,2-dihydro-2-oxo-5-(pyridinyl)nicotinamides, which are converted to the corresponding 3-amino compounds by reaction with a reagent capable of converting carbamyl to amino, e.g., by heating with an alkali metal hypohalite. A preferred embodiment of these compounds is 3-amino-5-(4-pyridinyl)-2(1H)-pyridinone, now generically known as amrinone and alternatively named 5-amino-[3,4'-bipyridin]-6(1H)-one. One method shown for preparing the 3-cyano-5-(pyridinyl)-2(1H)-pyridinones, alternatively named 1,2-dihydro-2-oxo-5-(pyridinyl)nicotinonitriles, is the reaction of α-(pyridinyl)-β-(dialkylamino)acrolein with α-cyanoacetamide. U.S. Pat. No. 4,072,746 also shows 3-Q-5-(pyridinyl)-2(1H)-pyridinones where Q is hydrogen, halo, lower-alkylamino, di-(lower-alkyl)amino or NHAc where Ac is lower-alkanoyl or lower-carbalkoxy. The disclosure of U.S. Pat. No. 4,072,746 also is shown in Lesher and Opalka U.S. Pat. Nos. 4,107,315, 4,137,233, 4,199,586 and 4,225,715.

Lesher and Philion [U.S. Pat. No. 4,313,951, issued Feb. 2, 1982] show as cardiotonic agents 3-amino(or cyano or carbamyl)-6-(lower-alkyl)-5-(pyridinyl)-2(1H)-pyridinones.

Lesher and Singh [U.S. Pat. No. 4,297,362, issued Oct. 27, 1981] show as a cardiotonic agent 4-(3,4-diaminophenyl)pyridine or its salts.

Collins et al [U.S. Pat. No. 4,302,462, issued Nov. 24, 1981] show as cardiotonic agents 4-[4(or 3)-pyridinyl]-1,2-benzenediol and corresponding dimethyl ether.

PRIOR PUBLICATIONS

The following publications appeared prior to the filing of the instant application but subsequent the filing of parent applications Ser. Nos. 248,840 and 300,294 and subsequent to completion of applicants' invention disclosed and claimed herein: Sandoz AG Patent Cooperation Treaty Application No. 81/02575, published Sept. 17, 1981, and corresponding U.K. patent applications No. 2,070,606, published Sept. 9, 1981, which disclose, inter alia, as cardiotonic agents and claim selected 3-amino-6-$R_2$-5-aryl-2(1H)-pyridinones where $R_2$ is hydrogen or lower-alkyl and aryl is, inter alia, phenyl, 4-methoxyphenyl, 3-methoxyphenyl or 3,4-dimethoxyphenyl. These compounds are reportedly prepared from the corresponding 1,2-dihydro-2-oxo-6-$R_2$-5-arylnicotinamides, in turn, prepared from the corresponding 1,2-dihydro-2-oxo-6-$R_2$-5-arylnicotinonitriles.

SUMMARY OF THE INVENTION

In a composition of matter aspect, the invention resides in 3-amino-5-[3- and/or 4-(hydroxy and/or amino)-phenyl]-2(1H)-pyridinones, useful as cardiotonic agents.

A composition aspect of the invention resides in the cardiotonic composition for increasing cardiac contractility, said composition comprising a pharmaceutically acceptable carrier, and as the active component thereof, a cardiotonically effective amount of 3-amino-5-[3- and/or 4-(hydroxy and/or amino)-phenyl]-2(1H)-pyridinone or salt thereof.

A method aspect of the invention resides in the method for increasing cardiac contractility in a patient requiring such treatment which comprises administering a medicament comprising a pharmaceutically acceptable carrier and, as the active component, a cardiotonically effective amount of 3-amino-5-[3- and/or 4-(hydroxy and/or amino)-phenyl]-2(1H)-pyridinone or salt thereof.

In a process aspect the invention resides in the process for preparing 3-amino-5-[3-and/or 4-(hydroxy and/or amino)-phenyl]-2(1H)-pyridinone which comprises reacting the corresponding 3-carbamyl compound with a reagent capable of converting carbamyl to amino or, alternatively, which comprises first reacting a 3-carbamyl-5-[3- and/or 4-(lower-alkoxy and/or nitro)-phenyl]-2(1H)-pyridinone with a reagent capable of converting carbamyl to amino to produce the corresponding 3-amino-[3- and/or 4-(lower-alkoxy and/or nitro)-phenyl]-2(1H)-pyridinone and then reacting the latter compound with a reagent to convert lower-alkoxy to hydroxy or a reagent to convert nitro to amino.

In another composition of matter aspect, the invention resides in 3-amino-5-[3- or 4-methoxyphenyl or 3,4-dimethoxyphenyl]-2(1H)-pyridinones, useful as intermediates for preparing said 3-amino-5-[3-or 4-hydroxyphenyl or 3,4-dihydroxyphenyl]-2(1H)-pyridinones, useful as cardiotonic agents.

Another composition of matter aspect of the invention resides in 1,2-dihydro-2-oxo-5-(3-R$_2$-4-R$_3$-phenyl)-6-R-nicotinonitriles, which are useful as cardiotonic agents and as intermediates for the corresponding 3-amino-2(1H)-pyridinones of formula I, where R$_2$, R$_3$ and R are defined hereinbelow in Formula II.

Another composition aspect of the invention resides in the cardiotonic composition for increasing cardiac contractility, said composition comprising a pharmaceutically acceptable carrier, and as the active component thereof, a cardiotonically effective amount of 1,2-dihydro-2-oxo-5-[3- and/or 4-(hydroxy and/or amino)-phenyl]-6-R-nicotinonitrile, alternatively named 1-R$_1$-3-cyano-5-[3- and/or 4-(hydroxy and/or amino)-phenyl]-6-R-2(1H)-pyridinone, or salt thereof, where R$_1$ and R are defined as in formula I below or the corresponding compound where the 5-substituent is 4-hydroxy-3-nitrophenyl.

Another method aspect of the invention resides in the method for increasing cardiac contractility in a patient requiring such treatment which comprises administering a medicament comprising a pharmaceutically acceptable carrier and a cardiotonically effective amount of the active component of the cardiotonic composition described in the immediately preceding paragraph.

DETAILED DESCRIPTION INCLUSIVE OF PREFERRED EMBODIMENTS

A composition of matter aspect of the invention resides in a 1-R$_1$-3-amino-5-(3-R'-4-R''-phenyl)-6-R-2(1H)-pyridinone having formula I

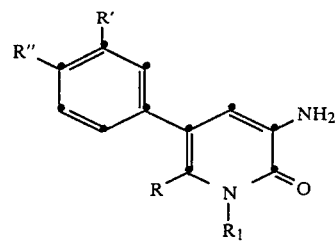

or acid-addition salt thereof, where R$_1$ is hydrogen, lower-alkyl or lower-hydroxyalkyl, R is hydrogen or lower-alkyl, R' and R'' are each hydrogen, amino or hydroxy at least one of R' or R'' being other than hydrogen. The compounds of formula I are useful as cardiotonics, as determined by standard pharmacological evaluation procedures. Preferred embodiments are those of formula I where R$_1$ is hydrogen, R is methyl or ethyl, R' is hydrogen, hydroxy or amino and R'' is hydroxy or hydrogen, the latter only when R' is other than hydrogen. A particularly preferred embodiment is 3-amino-5-(4-hydroxyphenyl)-6-methyl-2(1H)-pyridinone (R'' is hydroxy, R' and R$_1$ are each hydrogen and R is methyl) or acid-addition salt thereof.

A composition aspect of the invention resides in a cardiotonic composition for increasing cardiac contractility, said composition comprising a pharmaceutically acceptable carrier and, as the active component thereof, a cardiotonically effective amount of 1-R$_1$-3-amino-5-(3-R'-4-R''-phenyl)-6-R-2(1H)-pyridinone or pharmaceutically acceptable acid-addition salt thereof, where R$_1$, R, R' and R'' are each defined as in formula I. Preferred embodiments of this composition aspect of the invention are those where the active component is the compound of formula I where R$_1$ is hydrogen, R is methyl or ethyl, R' is hydrogen, hydroxy or amino and R'' is hydroxy or hydrogen, the latter only when R' is other than hydrogen. A particularly preferred embodiment is the composition having as the active component 3-amino-5-(4-hydroxyphenyl)-6-methyl-2(1H)-pyridinone or pharmaceutically acceptable acid-addition salt thereof.

A method aspect of the invention resides in the method for increasing cardiac contractility in a patient requiring such treatment which comprises administering orally or parenterally in a solid or liquid dosage form to such patient a composition comprising a pharmaceutically acceptable carrier and, as active component thereof, a cardiotonically effective amount of 1-R$_1$-3-amino-5-(3-R'-4-R''-phenyl)-6-R-2(1H)-pyridinone of pharmaceutically acceptable salt thereof, where R$_1$, R, R' and R'' are each defined as in formula I. Preferred embodiments of this method aspect of the invention are those where the active component is the same as the active component of preferred corresponding composition embodiments described in the immediately preceding paragraph.

A process aspect of the invention resides in the process for producing 1-R$_1$-3-amino-5-(3-R'-4-R''-phenyl)-6-R-2(1H)-pyridinone of formula I which comprises reacting the corresponding 1,2-dihydro-2-oxo-5-(3-R'-4-R''-phenyl)-6-R-nicotinamide with a reagent capable of converting carbamyl to amino. Alternatively, the compounds of formula I are prepared stepwise by first reacting said 1,2-dihydro-2-oxo-5-(3-R'-4-R''-phenyl)-6-R-nicotinamide where R' and/or R'' instead of being hydroxy and/or amino are/is respectively lower-alkoxy and/or nitro with a reagent capable of converting carbamyl to amino and then reacting the resulting corresponding 3-amino-2(1H)-pyridinone where R' and/or R'' are/is lower-alkoxy and/or nitro with a reagent capable of converting lower-alkoxy to hydroxy and/or with a reagent capable of converting nitro to amino. Preferred process embodiments are those which produce preferred composition of matter aspects noted hereinabove.

Another composition of matter aspect of the invention resides in a 1-$R_1$-3-amino-5-(3-R'-4-R''-phenyl)-6-R-2(1H)-pyridinone having formula I or acid-addition salt thereof, where $R_1$ is hydrogen, lower-alkyl or lower-hydroxyalkyl, R is hydrogen or lower-alkyl, R' and R'' are each hydrogen or methoxy at least one of R' or R'' being methoxy. These compounds are useful as intermediates for preparing the corresponding cardiotonically active compounds of formula I where at least one of R' or R'' is hydroxy. Preferred embodiments are those of formula I where $R_1$ is hydrogen, R is methyl or ethyl, R' is hydrogen or methoxy and R'' is methoxy or hydrogen, the latter only when R' is methoxy. A particularly preferred embodiment is 3-amino-5-(4-methoxyphenyl)-6-methyl-2(1H)-pyridinone or acid-addition salt thereof.

Another composition of matter aspect of the invention resides in 1-$R_1$-1,2-dihydro-2-oxo-5-(3-$R_2$-4-$R_3$-phenyl)-6-R-nicotinonitrile having formula II

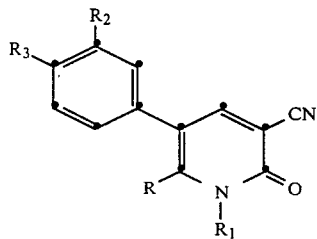

or acid-addition salt thereof, where $R_1$ is hydrogen, lower-alkyl or lower-hydroxyalkyl, R is hydrogen or lower-alkyl, $R_2$ and $R_3$ are each hydrogen, amino or hydroxy at least one of $R_2$ or $R_3$ being other than hydrogen or where $R_2$ is nitro and $R_3$ is hydroxy with the proviso that when R is methyl and $R_1$ and $R_2$ are simultaneously hydrogen, $R_3$ is other than amino, and with the further proviso that when R and $R_1$ are simultaneously hydrogen, at least one of $R_2$ and $R_3$ is other than hydroxy. The compounds of formula II are intermediates in the preparation of the corresponding 3-amino compounds of formula I and are useful as cardiotonics, as determined by standard pharmacological evaluation procedures. Preferred embodiments are those of formula II where $R_3$ is hydroxy, $R_2$ is hydrogen and R is hydrogen, methyl or ethyl, or where $R_3$ is hydroxy, $R_2$ is hydroxy, nitro or amino and R is methyl or ethyl.

A composition aspect of the invention resides in a cardiotonic composition for increasing cardiac contractility, said composition comprising a pharmaceutically acceptable carrier and, as the active component thereof, a cardiotonically effective amount of 1-$R_1$-1,2-dihydro-2-oxo-5-(3-$R_4$-4-$R_5$-phenyl)-6-R-nicotinonitrile having formula III

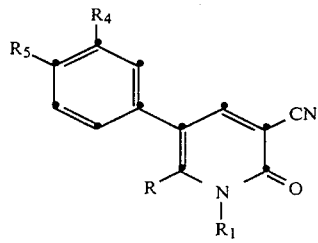

or pharmaceutically acceptable acid-addition salt thereof, where R and $R_1$ have the same meanings given for formula I, $R_4$ and $R_5$ have the same respective meanings as R' and R'' given for formula I or where $R_4$ is nitro and $R_5$ is hydroxy. Preferred embodiments of this composition aspect of the invention are those where the active component is the compound of formula III where $R_1$ is hydrogen, R is hydrogen, methyl or ethyl, $R_4$ is hydrogen, hydroxy or amino, and $R_5$ is hydroxy or hydrogen, the latter only when $R_4$ is other than hydrogen, or where $R_4$ is nitro, $R_5$ is hydroxy, $R_1$ is hydrogen and R is methyl or ethyl.

A method aspect of the invention resides in the method for increasing cardiac contractility in a patient requiring such treatment which comprises administering orally or parenterally in a solid or liquid dosage form to such patient a composition comprising a pharmaceutically acceptable carrier and, as active component thereof, a cardiotonically-effective amount of 1-$R_1$-1,2-dihydro-2-oxo-5-(3-$R_4$-4-$R_5$-phenyl)-6-R-nicotinonitrile of formula III hereinabove or pharmaceutically acceptable acid-addition salt thereof. Preferred embodiments of this method aspect of the invention are those where the active component is the same as the active component of the preferred composition embodiments described in the immediately preceding paragraph.

The term "lower-alkyl" as used herein, e.g., as one of the meanings of R and $R_1$ in formula I, II or III, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

The term "lower-hydroxyalkyl", as used herein, e.g., as one of the meanings for $R_1$ in formula I, II or III, means hydroxyalkyl radicals having from two to six carbon atoms and having its hydroxy group and its free valence bond (or connecting linkage) on different carbon atoms which can be arranged as straight or branched chains, illustrated by 2-hydroxyethyl, 2-hydroxypropyl, 3-hydroxypropyl, 2-hydroxy-2-methylpropyl, 2-hydroxy-1,1-dimethylethyl, 4-hydroxybutyl, 5-hydroxyamyl, 6-hydroxyhexyl, and the like.

The compounds of the invention having formula I, and those having formula II or III in which at least one of $R_2$ and $R_3$ in formula II or at least one of $R_4$ and $R_5$ in formula III is amino are useful both in the free base form and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base form of the cardiotonically active compounds of the invention are not vitiated by side effects ascribable to the anions. In practicing the invention, it is convenient to use the free base form; however, appropriate pharmaceutically acceptable salts within the scope of the invention are those derived from mineral acids such as hydrochloric acid, sulfuric acid, phosphoric acid, and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of the invention were assigned on the basis of evidence provided by infrared, nuclear magnetic resonance and mass spectra, and by the correspondence of calculated and found values for the elemental analyses.

The manner of making and using the instant invention will now be generally described so as to enable a person skilled in the art of pharmaceutical chemistry to make and use the same, as follows.

The conversion of 1-$R_1$-1,2-dihydro-2-oxo-5-(3-R'-4-R''-phenyl)-6-R-nicotinamide to the corresponding 3-amino-1-$R_1$-5-(3-R'-4-R''-phenyl)-6-R-2(1H)-pyridinone is carried out by reacting 1-$R_1$-1,2-dihydro-2-oxo-5-(3-R'-4-R''-phenyl)-6-R-nicotinamide with a reagent capable of converting carbamyl to amino. This reaction is conveniently run by first reacting an aqueous mixture containing an alkali metal hypohalite, preferably sodium or potassium hypobromite or hypochorite, with said substituted nicotinamide at about room temperature or below, next heating the reaction mixture and then acidifying it preferably with an aqueous mineral acid, e.g., hydrochloric acid. The reaction can be carried out from about 25° C. to 100° C., preferably about 60° C. to 100° C. The compounds of formula I also are prepared stepwise by first reacting the 1-$R_1$-1,2-dihydro-2-oxo-5-(3-R'-4-R''-phenyl)-6-R-nicotinamide where R' and/or R'' instead of being hydroxy and/or amino are/is lower-alkoxy and/or nitro respectively to produce the corresponding 3-amino compound where R' and/or R'' are/is lower-alkoxy and/or nitro and then converting lower-alkoxy to hydroxy and/or converting nitro to amino by generally known means as illustrated hereinbelow, e.g., Examples C-2 and C-4.

The preparation of the said intermediate 1-$R_1$-1,2-dihydro-2-oxo-5-(substituted-phenyl)-6-R-nicotinamides is carried out by generally known procedures as illustrated below in Examples B-1 through B-31, one such procedure being partial hydrolysis of the corresponding generally known 1-$R_1$-1,2-dihydro-2-oxo-5-(substituted-phenyl)-6-R-nicotinonitriles.

The cardiotonically active 1,2-dihydro-2-oxo-5-(substituted-phenyl)-6-R-nicotinonitriles of formulas II or III are prepared by reacting a compound of the formula IV or V

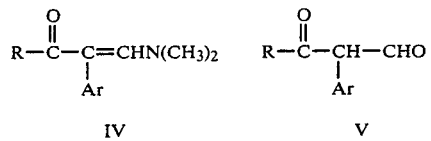

where R is hydrogen or lower-alkyl and Ar is 3-$R_2$-4-$R_3$-phenyl as defined in formula II or 3-$R_4$-4-$R_5$-phenyl as defined in formula III, with N-$R_1$-α-cyanoacetamide. The reaction of IV with N-$R_1$-α-cyanoacetamide is carried out preferably by heating the reactants at about 65° to 150° C. in a suitable solvent in the presence of a basic condensing agent. The reaction is conveniently run using an alkali metal lower-alkoxide, preferably sodium methoxide or ethoxide, in a lower-alkanol, e.g., methanol or ethanol, or in an aprotic solvent such as dimethylformamide. Other basic condensing agents include sodium hydride, lithium diethylamide, and the like. Other aprotic solvents include tetrahydrofuran, acetonitrile, ether, benzene, dioxane, and the like. The reaction mixture is acidified and the product isolated. The reaction of V with N-$R_1$-α-cyanoacetamide is carried out preferably by heating at about 65° to 150° C. in the presence of a condensing agent, preferably morpholine or piperidine and/or its acetate. The reaction is conveniently carried out by refluxing a benzene solution containing the reactants in the presence of morpholine, piperidine, morpholine acetate, piperidine acetate or mixtures thereof, preferably with a water separator attached to the reaction vessel to collect the water produced by the reaction. The reaction also can be run using other solvents such as those shown above in the reaction of IV with N-$R_1$-α-cyanoacetamide. The above reactions preferably are carried out using α-cyanoacetamide and IV or V where Ar is 4-methoxy-3-$R_2$(or $R_4$)-phenyl or 3,4-dimethoxyphenyl to produce the corresponding 1,2-dihydro-2-oxo-5-(4-methoxy-3-$R_2$(or $R_4$)-phenyl or 3,4-dimethoxyphenyl)-6-R-nicotinonitrile and then reacting said compound with a reagent capable of converting methoxy to hydroxy, e.g., hydrogen bromide, lithium iodide and collidine, and the like.

The preparation of the 1-$R_1$-1,2-dihydro-2-oxo-5-(substituted-phenyl)-6-R-nicotinonitriles (formulas II and III) used herein is illustrated below in Examples A-1 through A-31.

The following examples will further illustrate the invention without, however, limiting it thereto.

A.
1-R₁-1,2-DIHYDRO-2-OXO-5-(SUBSTITUTED-PHENYL)-6-R-NICOTINONITRILES

A-1. 1,2-Dihydro-5-(4-methoxyphenyl)-2-oxonicotinonitrile—To a stirred mixture containing 13.5 g. of sodium methoxide in 200 ml. of methanol was added 12.6 g. of cyanoacetamide and 20.5 g. of 3-dimethylamino-2-(4-methoxyphenyl)-2-propenal and the resulting mixture was heated with stirring on a steam bath for 12 hours. The reaction mixture was concentrated in vacuo to yield a yellow semi-solid material. This material was taken up with water and the resulting mixture (partial dissolution) was acidified with acetic acid. The separated solid was collected, washed with water, dried in vacuo, recrystallized from dimethylformamide and dried in vacuo for 24 hours at 0.01 mm. and 80° C. to produce 11.6 g. of 1,2-dihydro-5-(4-methoxyphenyl)-2-oxonicotinonitrile, m.p. 294°–295° C. with decomposition.

The intermediate 3-dimethylamino-2-(4-methoxyphenyl)-2-propenal was prepared by the procedure described in the second paragraph of Example B-5 but using 4-methoxyphenylacetic acid in place of 3,4-dimethoxyphenylacetic acid.

A-2. 1,2-Dihydro-5-(4-hydroxyphenyl)-2-oxonicotinonitrile—To a mixture containing 11.3 g. of 1,2-dihydro-5-(4-methoxyphenyl)-2-oxonicotinonitrile in 110 ml. of collidine was added 36.8 g. of anhydrous lithium iodide and the resulting mixture was refluxed with stirring under nitrogen for 24 hours. The reaction mixture was cooled, treated with ice and acidified with 6N hydrochloric acid and cooled. The precipitated solid was collected and dried in vacuo to yield a 8.5 g. of 1,2-dihydro-5-(4-hydroxyphenyl)-2-oxonicotinonitrile. The product obtained herein was combined with another sample obtained by comparable run and the combined material was recrystallized from dimethylformamide-methanol and dried at 0.01 mm. and 100° C. for 7 days to produce 13.47 g. of 1,2-dihydro-5-(4-hydroxyphenyl)-2-oxonicotinonitrile, m.p. >300° C.

A-3. 1,2-Dihydro-5-(4-nitrophenyl)-2-oxonicotinonitrile, m.p. 339°–346° C. with decomposition, 87.2 g., was obtained following the procedure described in Example A-1 using 83 g. of 3-dimethylamino-2-(4-nitrophenyl)-2-propenal, 50.4 g. of cyanoacetamide, 54 g. of sodium methoxide and 1500 ml. of methanol.

A-4. 5-(4-Aminophenyl)-1,2-dihydro-2-oxonicotinonitrile—A mixture containing 14.47 g. of 1,2-dihydro-5-(4-nitrophenyl)-2-oxonicotinonitrile, 1.0 g. of 10% palladium-on-charcoal, 300 ml. of dimethylformamide and 5.76 g. (3.9 ml.) of methanesulfonic acid was treated under catalytic hydrogenation conditions until the theoretical quantity of hydrogen to reduce nitro to amino was taken up. The reaction mixture was filtered thru diatomaceous earth to remove the catalyst. The filtrate was concentrated in vacuo to a volume of about 200 ml. and to the concentrate was added slowly 3.9 ml. (5.76 g.) of methanesulfonic acid, the mixture stirred for about 10 minutes and then treated with about 500 ml. of methylene dichloride. The crystalline solid was collected, dissolved in about 900 ml. of hot methanol, the hot solution treated with decolorizing charcoal and then filtered thru a sintered glass funnel. The filtrate was cooled and the separated crystalline material was collected and recrystallized from methanol. The resulting product was dissolved in 150 ml. of warm 2N hydrochloric acid, the solution basified with aqueous sodium hydroxide solution and cooled. The resulting white solid was collected, dissolved in 400 ml. of methanol, treated with 2 ml. of methanesulfonic acid, the mixture concentrated to remove the solvent and recrystallized twice from methanol, filtering the hot yellow solution thru a sintered glass funnel and concentrating the filtrate to a volume of about 200 ml., cooling, collecting the solid and drying it in vacuo at 80° C., to yield 6.1 g. of 5-(4-aminophenyl)-1,2-dihydro-2-oxonicotinonitrile as its monomethanesulfonate, m.p. 252°–260° C.

A-5. 1,2-Dihydro-5-(4-methoxyphenyl)-6-methyl-2-oxonicotinonitrile—A mixture containing 100 g. of 97% 3-(4-methoxyphenyl)propan-2-one, 94.2 ml. of dimethylformamide dimethyl acetal and 500 ml. of dimethylformamide was stirred at room temperature for over 17 hours and then on a steam bath for 2 hours. There was then added 23.6 ml. of dimethylformamide dimethyl acetal followed by stirring at room temperature for about 75 minutes and then on a steam bath for about 2½ hours. To the partially cooled solution containing 4-dimethyl-amino-3-(4-methoxyphenyl)-3-buten-2-one was added 79.8 g. of sodium methoxide and 74.5 g. of cyanoacetamide and the resulting mixture was heated on a steam bath with stirring for about 12 hours. The reaction mixture was then diluted with about 1.5 l. of water and the resulting suspension was acidified with acetic acid. The separated solid was collected and recrystallized from dimethylformamide-water to yield 116.8 g of 1,2-dihydro-5-(4-methoxyphenyl)-6-methyl-2-oxonicotinonitrile, m.p. 253°–255°. A sample of this material was further purified by recrystallizing successively from methanol and acetic acid-water and drying at 90°–95° C., in vacuo for over 24 hours to yield said product, m.p. 258°–259° C.

A-6. 1,2-Dihydro-5-(4-hydroxyphenyl)-6-methyl-2-oxonicotinonitrile, m.p. 275°–276° C. with decomposition, was prepared following the procedure described in Example A-2 using 12.0 g. of 1,2-dihydro-5-(4-methoxyphenyl)-6-methyl-2-oxonicotinonitrile, 36.8 g. of lithium iodide and 120 ml. of collidine.

Following the procedure described in Example A-1 but using in place of 3-dimethylamino-2-(4-methoxyphenyl)-2-propenal a molar equivalent quantity of the appropriate 3-dimethylamino-2-(substituted-phenyl)-2-propenal, it is contemplated that the corresponding 1,2-dihydro-2-oxo-5-(substituted-phenyl)nicotinonitriles of Examples A-7 through A-11 can be obtained.

A-7. 1,2-dihydro-5-(3-methoxyphenyl)-2-oxonicotinonitrile.

A-8. 1,2-Dihydro-5-(3,4-dimethoxyphenyl)-2-oxonicotinonitrile.

A-9. 1,2-Dihydro-5-(3-nitrophenyl)-2-oxonicotinonitrile.

A-10. 1,2-Dihydro-5-(3,4-dinitrophenyl)-2-oxonicotinonitrile.

A-11. 1,2-Dihydro-5-(4-methoxy-3-nitrophenyl)-2-oxonicotinonitrile.

The intermediate 3-dimethylamino-2-(substituted-phenyl)-2-propenals used in Examples A-7 through A-11 are either known or are readily prepared from known compounds by conventional means, e.g., by reacting substituted-phenylacetic acid with the reaction product obtained by reacting dimethylformamide with a phosphorus oxyhalide, preferably the oxychloride or oxybromide, as illustrated hereinbelow in the second paragraph of Example B-5.

Following the procedure described in Example A-2 or A-4 but using in place of 1,2-dihydro-5-(4-methoxyphenyl or 4-nitrophenyl)-2-oxonicotinonitrile a molar equivalent quantity of the appropriate 1,2-dihydro-5-(substituted-phenyl)-2-oxonicotinonitrile, it is contemplated that the corresponding compounds of Examples A-12 through A-16 can be obtained.

A-12. 1,2-Dihydro-5-(3-hydroxyphenyl)-2-oxonicotinonitrile using the procedure of Example A-2.

A-13. 1,2-Dihydro-5-(3,4-dihydroxyphenyl)-2-oxonicotinonitrile using the procedure of Example A-2.

A-14. 1,2-Dihydro-5-(4-methoxy-3-aminophenyl)-2-oxonicotinonitrile using the procedure of Example A-4.

A-15. 1,2-Dihydro-5-(3-aminophenyl)-2-oxonicotinonitrile using the procedure of Example A-4.

A-16. 1,2-Dihydro-5-(3,4-diaminophenyl)-2-oxonicotinonitrile using the procedure of Example A-4.

Following the procedure described in Example A-5 but using in place of 3-(4-methoxyphenyl)propan-2-one a molar equivalent quantity of the appropriate 3-(substituted-phenyl)propan-2-one or substituted-benzyl lower-alkyl ketone, it is contemplated that the corresponding 1,2-dihydro-2-oxo-5-(substituted-phenyl)-6-methyl(or lower-alkyl)-nicotinonitriles of Examples A-17 to A-21 can be obtained.

A-17. 1,2-Dihydro-5-(3-methoxyphenyl)-6-methyl-2-oxonicotinonitrile, m.p. 247°–250° C., starting with 3-(3-methoxyphenyl)propan-2-one.

A-18. 1,2-Dihydro-5-(3,4-dimethoxyphenyl)-6-methyl-2-oxonicotinonitrile, m.p. 262°–263° C., starting with 3-(3,4-dimethoxyphenyl)propan-2-one via 4-dimethylamino-3-(3,4-dimethoxyphenyl)-3-buten-2-one, m.p. 94°–95.5° C. (prepared as in Example A-5).

A-19. 1,2-Dihydro-5-(4-nitrophenyl)-6-methyl-2-oxonicotinonitrile, starting with 3-(4-nitrophenyl)propan-2-one.

A-20. 1,2-Dihydro-5-(4-methoxyphenyl)-6-ethyl-2-oxonicotinonitrile, starting with 1-(4-methoxyphenyl)-butan-2-one.

A-21. 1,2-Dihydro-5-(4-methoxy-3-nitrophenyl)-6-methyl-2-oxonicotinonitrile, m.p. >300° C., starting with 3-(4-methoxy-3-nitrophenyl)propan-2-one. Alternatively, 1,2-dihydro-5-(4-methoxy-3-nitrophenyl)-6-methyl-2-oxonicotinonitrile was prepared by nitrating 1,2-dihydro-5-(4-methoxyphenyl)-6-methyl-2-oxonicotinonitrile by heating it with concentrated nitric acid in acetic acid on a steam bath for two hours and then pouring the reaction mixture into water and collecting the product.

Following the procedure described in Example A-2 or A-4 but using in place of 1,2-dihydro-5-(4-methoxyphenyl or 4-nitrophenyl)-2-oxonicotinonitrile a molar equivalent quantity of the appropriate 1,2-dihydro-5-(substituted-phenyl)-6-(lower-alkyl)-2-oxonicotinonitrile, it is contemplated that the corresponding compounds of Examples A-22 through A-27 can be obtained.

A-22. 1,2-Dihydro-5-(3-hydroxyphenyl)-6-methyl-2-oxonicotinonitrile, using 1,2-dihydro-5-(3-methoxyphenyl)-6-methyl-2-oxonicotinonitrile and the procedure of Example A-2.

A-23. 1,2-Dihydro-5-(3,4-dihydroxyphenyl)-6-methyl-2-oxonicotinonitrile, m.p. 267° C. (chars), using 1,2-dihydro-5-(3,4-dimethoxyphenyl)-6-methyl-2-oxonicotinonitrile and the procedure of Example A-2.

A-24. 1,2-Dihydro-5-(4-aminophenyl)-6-methyl-2-oxonicotinonitrile, using 1,2-dihydro-5-(4-nitrophenyl)-6-methyl-2-oxonicotinonitrile and the procedure of Example A-4.

A-25. 1,2-Dihydro-5-(4-hydroxyphenyl)-6-ethyl-2-oxonicotinonitrile, using 1,2-dihydro-5-(4-methoxyphenyl)-6-ethyl-2-oxonicotinonitrile and the procedure of Example A-2.

A-26. 1,2-Dihydro-5-(4-hydroxy-3-nitrophenyl)-6-methyl-2-oxonicotinonitrile, m.p. 290°–293° C., using 1,2-dihydro-5-(4-methoxy-3-nitrophenyl)-6-methyl-2-oxonicotinonitrile and the procedure of Example A-2.

A-27. 1,2-Dihydro-5-(3-amino-4-hydroxyphenyl)-6-methyl-2-oxonicotinonitrile, using 1,2-dihydro-5-(4-hydroxy-3-nitrophenyl)-6-methyl-2-oxonicotnonitrile and the procedure of Example A-4 or using 1,2-dihydro-5-(4-methoxy-3-aminophenyl)-6-one-2-oxonicotinonitrile and the procedure of Example A-2.

Following the procedure described in Example A-5 but using in place of cyanoacetamide a molar equivalent quantity of the appropriate N-$R_1$-cyanoacetamide, it is contemplated that the corresponding 1-$R_1$-1,2-dihydro-5-(4-methoxyphenyl)-6-R-2-oxonicotinonitriles of Examples A-28 and A-29 can be obtained.

A-28. 1,2-Dihydro-5-(4-methoxyphenyl)-1,6-dimethyl-2-oxonicotinonitrile, using N-methylcyanoacetamide.

A-29. 1,2-Dihydro-1-(2-hydroxyethyl)-5-(4-methoxyphenyl)-6-methyl-2-oxonicotinonitrile, using N-(2-hydroxyethyl)cyanoacetamide.

Following the procedure described in Example A-2 but using in place of 1,2-dihydro-5-(4-methoxyphenyl)-2-oxonicotinonitrile a molar equivalent quantity of the appropriate 1-$R_1$-1,2-dihydro-5-(4-methoxyphenyl)-6-(lower-alkyl)-2-oxonicotinonitrile, it is contemplated that the corresponding compounds of Examples A-30 and A-31 can be obtained.

A-30. 1,2-Dihydro-5-(4-hydroxyphenyl)-1,6-dimethyl-2-oxonicotinonitrile.

A-31. 1,2-Dihydro-1-(2-hydroxyethyl)-5-(4-hydroxyphenyl)-6-methyl-2-oxonicotinonitrile.

B.

1-$R_1$-1,2-DIHYDRO-2-OXO-5-(SUBSTITUTED-PHENYL)-6-R-NICOTINAMIDES

B-1. 1,2-Dihydro-5-(4-methoxyphenyl)-2-oxonicotinamide—A mixture containing 82.1 g. of 3-dimethylamino-2-(4-methoxyphenyl)-2-propenal, 63.15 g. of malonamide (97%), 54.0 g. of sodium methoxide and 800 ml. of methanol was refluxed with stirring for about 17 hours and chilled. The reaction mixture was filtered and the filtrate concentrated in vacuo to a volume of about 500 ml., acidified with acetic acid and chilled. The resulting solid was collected, dried at 90° C. in a vacuum oven to yield 25.25 g. of 1,2-dihydro-5-(4-methoxyphenyl)-2-oxonicotinamide, m.p. 283°–286° C.

B-2. 1,2-Dihydro-5-(4-nitrophenyl)-2-oxonicotinamide—A mixture containing 1,2-dihydro-5-(4-nitrophenyl)-2-oxonicotinonitrile and 1 liter of 90% sulfuric acid was stirred at room temperature for about 3 hours, allowed to stand at room temperature overnight (about 15 hours) and then stirred on a steam bath for about 2 hours. The reaction mixture was partially cooled and then quenched in a mixture of 2.5 liters of ice-water. The solid that separated was collected, washed with water, suspended in 5% aqueous potassium carbonate solution sufficient to impart weak alkalinity to the suspension. The suspension was stirred and the solid was collected, washed with water and dried at 90° C. in a vacuum oven to yield 103.7 g. of 1,2-dihydro-5-(4-nitrophenyl)-2-oxonicotinamide, m.p. >340° C.

B-3. 5-(4-Aminophenyl)-1,2-dihydro-2-oxonicotinamide—A mixture containing 1,2-dihydro-5-(4-nitrophenyl)-2-oxonicotinamide, 200 ml. of acetic acid and 0.20 g. of platinum dioxide was catalytically hydrogenated at room temperature for a period of 20 hours. The reaction mixture was filtered and the filter cake washed well with warm dimethylformamide; the filter cake was saved for further treatment described below. The combined acetic acid filtrate and dimethylformamide washings were concentrated in vacuo. The residue was taken up in isopropyl alcohol, the solution was acidified with hydrogen chloride in ethanol and then was diluted with ether and cooled. The separated product was collected and dried as below to yield 3.44 g. of 5-(4-aminophenyl)-1,2-dihydro-2-oxonicotinamide as its hydrochloride, m.p. >315° C. More product was obtained from the original filter cake (supra) by successively extracting it with hydrogen chloride in warm ethanol and then hot dimethylformamide. To the combined extracts was added excess ethanolic-hydrogen chloride, the solution was concentrated to a volume of less than 150 ml. and diluted with ether to precipitate the product; this was collected and dried in a vacuum oven at 90° C. to produce another 3.72 g. of 5-(4-aminophenyl)-1,2-dihydro-2-oxonicotinamide, m.p. >315° C. The combined samples of product, (7.16 g.), were dissolved in dilute hydrochloric acid and the solution treated with 10% potassium bicarbonate solution. The separated product was collected and dried at 90° C. in a vacuum oven to produce 1.07 g. of 5-(4-aminophenyl)-1,2-dihydro-2-oxonicotinamide containing ¼ mole of water per mole of product, m.p. >315° C.

B-4. 1,2-Dihydro-5-(4-methoxyphenyl)-6-methyl-2-oxonicotinamide—A 20.0 g. portion of 1,2-dihydro-5-(4-methoxyphenyl)-6-methyl-2-oxonicotinonitrile was added to 200 g. of polyphosphoric acid and the resulting mixture was heated with stirring on a steam bath overnight. The reaction mixture was added with stirring to about 200 ml. of ice-water mixture. The resulting mixture was made alkaline with ammonium hydroxide. The resulting solid was collected, air-dried, recrystallized from dimethylformamide and dried in vacuo at 100° C. and 0.01 mm. to yield 9.0 g. of 1,2-dihydro-5-(4-methoxyphenyl)-6-methyl-2-oxonicotinamide, m.p. >300° C.

B-5. 1,2-Dihydro-5-(3,4-dimethoxyphenyl)-2-oxonicotinamide—A mixture containing 235 g. of 2-(3,4-dimethoxyphenyl)-3-dimethylamino-2-propenal, 2 liters of methanol, 108 g. of sodium methoxide and 150 g. of malonamide was refluxed with stirring for about 30 minutes and the reaction mixture heated in vacuo to remove the solvent. The residue was dissolved in water and neutralized with acetic acid. The separated solid was collected, washed with water, dried, recrystallized from dimethylformamide and dried at 70° C. to yield 81 g. of 1,2-dihydro-5-(3,4-dimethoxyphenyl)-2-oxonicotinamide. A 20 g. sample of the material was recrystallized a second time from dimethylformamide to yield 16 g. of the product, m.p. 266°–268° C.

The intermediate 2-(3,4-dimethoxyphenyl)-3-dimethylamino-2-propenal was prepared as follows: To a chilled 1260 ml. portion of dimethylformamide was added dropwise 230 ml. of phosphorus oxychloride followed by addition of 196 g. of α-(3,4-dimethoxyphenyl)acetic acid. The reaction mixture was heated at about 70° C. on a steam bath for 3 hours, allowed to cool and then concentrated in vacuo to remove the solvent and excess volatile reactants. The resulting product was used directly in the above procedure.

Following the procedure described in Example B-1 but using in place of 3-dimethylamino-2-(4-methoxyphenyl)-2-propenal a molar equivalent quantity of the appropriate 3-dimethylamino-2-(substituted-phenyl)-2-propenal, it is contemplated that the corresponding 1,2-dihydro-2-oxo-5-(substituted-phenyl)nicotinamides of Examples B-6 through B-10 can be obtained.

B-6. 1,2-Dihydro-5-(3-methoxyphenyl)-2-oxonicotinamide.

B-7. 1,2-Dihydro-5-(3,4-diethoxyphenyl)-2-oxonicotinamide.

B-8. 1,2-Dihydro-5-(3-nitrophenyl)-2-oxonicotinamide.

B-9. 1,2-Dihydro-5-(3,4-dinitrophenyl)-2-oxonicotinamide.

B-10. 1,2-Dihydro-5-(4-methoxy-3-nitrophenyl)-2-oxonicotinamide.

Following the procedure described in Example A-2 or B-3 but using in place of 1,2-dihydro-5-(4-methoxyphenyl)-2-oxonicotinonitrile or 1,2-dihyro-5-(4-nitrophenyl)-2-oxonicotinamide respectively a molar equivalent quantity of the appropriate 1,2-dihydro-5-(substituted-phenyl)-2-oxonicotinamide, it is contemplated that the corresponding compounds of Examples B-11 through B-15 can be obtained.

B-11. 1,2-Dihydro-5-(3-hydroxyphenyl)-2-oxonicotinamide using the procedure of Example A-2.

B-12. 1,2-Dihydro-5-(3,4-dihydroxyphenyl)-2-oxonicotinamide using the procedure of Example A-2.

B-13. 1,2-Dihydro-5-(4-methoxy-3-aminophenyl)-2-oxonicotinamide using the procedure of Example B-3.

B-14. 1,2-Dihydro-5-(3-aminophenyl)-2-oxonicotinamide using the procedure of Example B-3.

B-15. 1,2-Dihydro-5-(3,4-diaminophenyl)-2-oxonicotinamide using the procedure of Example B-3.

Following the procedure described in Example B-4 but using in place of 1,2-dihydro-5-(4-methoxyphenyl)-6-methyl-2-oxonicotinonitrile a molar equivalent quantity of the appropriate 1,2-dihydro-5-(substituted-phenyl)-6-(lower-alkyl)nicotinonitrile, it is contemplated that the corresponding 1,2-dihydro-2-oxo-5-(substituted-phenyl)-6-(lower-alkyl)nicotinamides of Examples B-16 through B-22 can be obtained.

B-16. 1,2-Dihydro-5-(3-methoxyphenyl)-6-methyl-2-oxonicotinamide, m.p. 298°–300° C.

B-17. 1,2-Dihydro-5-(3,4-dimethoxyphenyl)-6-methyl-2-oxonicotinamide, m.p. >300° C.

B-18. 1,2-Dihydro-5-(4-nitrophenyl)-6-methyl-2-oxonicotinamide.

B-19. 1,2-Dihydro-5-(4-methoxyphenyl)-6-ethyl-2-oxonicotinamide.

B-20. 1,2-Dihydro-5-(4-methoxy-3-nitrophenyl)-6-methyl-2-oxonicotinamide.

B-21. 1,2-Dihydro-5-(4-hydroxy-3-nitrophenyl)-6-methyl-2-oxonicotinamide.

B-22. 1,2-Dihydro-5-(3-amino-4-hydroxyphenyl)-6-methyl-2-oxonicotinamide.

Following the procedure described in Example A-2 or B-3 but using in place of 1,2-dihydro-5-(4-methoxyphenyl)-2-oxonicotinonitrile or 1,2-dihydro-5-(4-nitrophenyl)-2-oxonicotinamide respectively a molar equivalent quantity of the appropriate 1,2-dihydro-5-(substituted-phenyl)-6-(lower-alkyl)-2-oxonicotinamide, it is contemplated that the corresponding compounds of Examples B-23 through B-27 can be obtained.

B-23. 1,2-Dihydro-5-(3-hydroxyphenyl)-6-methyl-2-oxonicotinamide.

B-24. 1,2-Dihydro-5-(3,4-dihydroxyphenyl)-6-methyl-2-oxonicotinamide.

B-25. 1,2-Dihydro-5-(4-aminophenyl)-6-methyl-2-oxonicotinamide.

B-26. 1,2-Dihydro-5-(4-hydroxyphenyl)-6-ethyl-2-oxonicotinamide.

B-27. 1,2-Dihydro-5-(3-amino-4-hydroxyphenyl)-6-methyl-2-oxonicotinamide.

Following the procedure described in Example B-2 but using in place of 1,2-dihydro-5-(4-nitrophenyl)-2-oxonicotinonitrile a molar equivalent quantity of the appropriate 1-$R_1$-1,2-dihydro-5-(substituted-phenyl)-6-R-2-oxonicotinonitrile, it is contemplated that the corresponding 1-$R_1$-1,2-dihydro-5-(substituted-phenyl)-6-R-2-oxonicotinamides of Examples B-28 through B-31 can be obtained.

B-28. 1,2-Dihydro-5-(4-methoxyphenyl)-1,6-dimethyl-2-oxonicotinamide.

B-29. 1,2-Dihydro-1-(2-hydroxyethyl)-5-(4-methoxyphenyl)-6-methyl-2-oxonicotinamide.

B-30. 1,2-Dihydro-5-(4-hydroxyphenyl)-1,6-dimethyl-2-oxonicotinamide.

B-31. 1,2-Dihydro-1-(2-hydroxyethyl)-5-(4-hydroxyphenyl)-6-methyl-2-oxonicotinamide.

C.
1-$R_1$-3-AMINO-5-(SUBSTITUTED-PHENYL)6-R-2(1H)-PYRIDINONES

C-1. 3-Amino-5-(4-methoxyphenyl)-2(1H)-pyridinone—To a cold solution containing 19.6 g. of sodium hydroxide in 450 ml. of water was added over a 20 minute period 4.92 ml. of bromine and the resulting mixture was stirred for about 15 additional minutes. To this solution containing sodium hypobromite was added 19.54 g. of 1,2-dihydro-5-(4-methoxyphenyl)-2-oxonicotinamide. The resulting reaction was stirred at room temperature for about 2 hours and then on a steam bath for an additional hour. The partially cooled suspension was acidified carefully with 6N hydrochloric acid and then neutralized with 2N potassium hydroxide solution. The resulting suspension was chilled and the solid product was collected by filtration. The solid was boiled with 600 ml. of isopropyl alcohol and the resulting solution diluted with 600 ml. of dimethylformamide. The resulting hot solution was concentrated to a volume 500 ml. and the resulting suspension was acidified with hydrogen chloride in ethanol. The resulting mixture was stirred, diluted with ether and the solid was collected by filtration and dried in a vacuum oven at 90° C. to yield 14.5 g. of product, m.p. 242°–246° C. A 5.64 g. portion of the product was dissolved in dimethylformamide and the solution treated with hydrogen chloride in ethanol to acidity. The separated product was collected and dried in vacuo in a vacuum oven at 90° C. to yield 3.92 g. of 3-amino-5-(4-methoxyphenyl)-2(1H)-pyridinone as its hydrochloride, m.p. 238°–242° C. with decomposition.

C-2. 3-Amino-5-(4-hydroxyphenyl)-2(1H)-pyridinone—A mixture containing 7.58 g. of 3-amino-5-(4-methoxyphenyl)-2(1H)-pyridinone, 90 ml. of 48% hydrogen bromide and 180 ml. of acetic acid was refluxed with stirring for about 8 hours. To the reaction mixture was added 108.9 g. of sodium acetate trihydrate in 300 ml. of water. The resulting suspension was stirred and then concentrated in vacuo to remove volatile materials. The remaining residue was mixed well with water; the solid material was collected by filtration and washed with water. The solid was taken up in about 300 ml. of water and the aqueous mixture was treated with an excess of 2N potassium hydroxide solution and the resulting mixture filtered through diatomaceous earth. The filtrate was acidified with acetic acid, the separates solid was collected and dried at 100° C. in a vacuum oven to produce 6 g. of 3-amino-5-(4-hydroxyphenyl)-2(1H)-pyridinone, m.p. 322°–326° C. with decomposition.

Acid-addition salts of 3-amino-5-(4-hydroxyphenyl)-2(1H)-pyridinone are conveniently prepared by adding to a mixture of 1 g. of 3-amino-5-(4-hydroxyphenyl)-2(1H)pyridinone in about 20 ml. of aqueous methanol the appropriate acid, e.g., hydrochloric acid, methanesulfonic acid, sulfuric acid, to a pH of about 2–3, chilling the mixture after partial evaporation and collecting the precipitated salt, e.g., hydrochloride, methanesulfonate, sulfate, respectively. Also, the lactate or hydrochloride acid-addition salt of 3-amino-5-(4-hydroxyphenyl)-2(1H)-pyridinone is conveniently prepared in aqueous solution by adding to water with stirring molar equivalent quantities each of 3-amino-5-(4-hydroxyphenyl)-2(1H)-pyridinone and lactic acid or hydrochloric acid, respectively.

C-3. 3-Amino-5-(4-nitrophenyl)-2(1H)-pyridinone, m.p. 260°–267° C. as its monohydrochloride ¼ hydrate, 14.77 g., ws prepared following the procedure described in Example C-1 using 25.92 g. of 1,2-dihydro-5-(4-nitrophenyl)-2-oxonicotinamide, 24.0 g. of sodium hydroxide, 6.15 ml. of bromine and 600 ml. of water.

C-4. 3-Amino-5-(4-aminophenyl)-2(1H)-pyridinone—A mixture containing 10.7 g. of 3-amino-5-(4-nitrophenyl)-2(1H)-pyridinone as its monohydrochloride, 1 g. of 10% palladium-on-charcoal and 300 ml. of dimethylformamide was treated under catalytic hydrogenation conditions, the reaction mixture was filtered to remove the catalyst and the filtrate was acidified with 100 ml. of 1.4M ethanolic hydrogen chloride. The solvent was distilled off in vacuo and the residue was treated with hot isopropyl alcohol. The insoluble material was collected, dissolved in about 300 ml. of methanol, treated with decolorizing charcoal, filtered and the filtrate concentrated to a volume of about 150 ml. The concentrated solution was cooled in ice and the separated product was collected and dried to yield 5.70 g. of 3-amino-5-(4-aminophenyl)-2(1H)pyridinone as its dihydrochloride dihydrate, m.p. 280°–287° C. with decomposition.

C-5. 3-Amino-5-(4-methoxyphenyl)-6-methyl-2(1H)pyridinone, m.p. 241°–243° C. with decomposition as its ¼ hydrate, was prepared following the procedure described above in Example C-1 using 22.9 g. of 1,2-dihydro-5-(4-methoxyphenyl)-6-methyl-2-oxonicotinamide, 23.9 g. sodium hydroxide dissolved in 450 ml. of water and 5.6 ml. of bromine and purification via its N-acetyl derivative described as follows. A total of 26.7 g. of 3-amino-5-(4-methoxyphenyl)-6-methyl-2(1H)-pyridinone prepared in several runs (and containing a small amount of unreacted 3-carbamyl starting material as determined by nmr) was refluxed with stirring with a mixture of 270 ml. of pyridine an 13.6 ml. of acetic anhydride. The reaction mixture was cooled, diluted with about 500 ml. of ether and the solid that separated was collected by filtration, washed with ether and dried in vacuo to yield 20.13 g. of 3-acetamido-5-(4-methoxyphenyl)-6-methyl-2(1H)-pyridinone. A 19.75 g. portion of said 3-acetamido compound in 200 ml. of 6N hydrochloric acid was refluxed with stirring for 32 hours (some ether cleavage here; see below). The reaction mixture was filtered and the filtrate made alkaline with ammonium hydroxide solution while cooling. The separated solid was collected by filtration, washed with water and dried. The solid was then taken up in about 100 ml. of 10% aqueous sodium hydroxide solution and the mixture stirred at room temperature for about 1 hour. The solid was collected, washed with water and dried in vacuo. The basic filtrate thus obtained was saved and used hereinbelow in Example C-6. The solid was again stirred with 100 ml. of 10% sodium hydroxide solution at room temperature for about 3 hours and again collected, washed with water and dried in vacuo to produce 5.31 g. of 3-amino-5-(4-methoxyphenyl)-6-methyl-2(1H)-pyridinone as its ¼ hydrate, m.p. 241°–243° C. with decomposition.

C-6. 3-Amino-5-(4-hydroxyphenyl)-6-methyl-2(1H)-pyridinone—The basic filtrate obtained from the previous example, C-5, was acidified with glacial acetic acid and cooled. The solid was collected by filtration, washed with water, dried in vacuo and then again taken up in about 100 ml. of 10% aqueous sodium hydroxide solution. The mixture was filtered to remove a small amount of insoluble material and the filtrate was acidified with glacial acetic acid. The solid that separated was collected by filtration, washed with water and dried in vacuo to yield 2.56 g. of 3-amino-5-(4-hydroxyphenyl)-6-methyl-2(1H)-pyridinone, m.p. 256°–257° C. with decomposition.

Acid-addition salts of 3-amino-5-(4-hydroxyphenyl)-6-methyl-2(1H)-pyridinone are conveniently prepared by adding to a mixture of 1 g. of 3-amino-5-(4-hydroxyphenyl)-6-methyl-2(1H)-pyridinone and about 20 ml. of aqueous methanol the appropriate acid, e.g., hydrochloric acid, methanesulfonic acid, sulfuric acid, to a pH of about 2–3, chilling the mixture after partial evaporation and collecting the precipitated salt, e.g., hydrochloride, methanesulfonate, sulfate, respectively. Also, the lactate or hydrochloride acid-addition salt of 3-amino-5-(4-hydroxphenyl)-6-methyl-2(1H)-pyridinone is conveniently prepared in aqueous solution by adding to water with stirring molar equivalent quantities each of 3-amino-5-(4-hydroxyphenyl)-6-methyl-2(1H)-pyridinone and lactic acid or hydrochloric acid, respectively.

C-7. 3-Amino-5-(3,4-dimethoxyphenyl)-2(1H)-pyridinone, m.p. 208°–215° C., 5 g., was prepared following the procedure described in Example C-1 using 14 g. of 1,2-dihydro-5-(3,4-dimethoxyphenyl)-2-oxonicotinamide, 270 ml. of water, 12 g. of sodium hydroxide and 3.1 ml. of bromine.

C-8. 3-Amino-5-(3,4-dihydroxyphenyl)-2(1H)pyridinone, m.p. 271°–274° C. as its hemihydrate, 11 g., was prepared following the procedure described in Example C-2 using 36 g. of 3-amino-5-(3,4-dimethoxyphenyl)-2(1H)-pyridinone, 180 ml. of 48% of hydrogen bromide, 400 ml. of acetic acid and recrystallization from dimethylformamide.

Following the procedure described in Example C-1 but using in place of 1,2-dihydro-5-(4-methoxyphenyl)-2-oxonicotinamide a molar equivalent quantity of the appropriate 1,2-dihydro-5-(substituted-phenyl)-2-oxonicotinamide, it is contemplated that the corresponding 3-amino-5-(substituted-phenyl)2(1H)-pyridinones of Examples C-9 through C-13 can be obtained.

C-9. 3-Amino-5-(3-methoxyphenyl)-2(1H)-pyridinone.

C-10. 3-Amino-5-(3,4-diethoxyphenyl)-2(1H)-pyridinone.

C-11. 3-Amino-5-(3-nitrophenyl)-2(1H)-pyridinone.

C-12. 3-Amino-5-(3,4-dinitrophenyl)-2(1H)-pyridinone.

C-13. 3-Amino-5-(4-methoxy-3-nitrophenyl)-2(1H)-pyridinone.

Following the procedure described in Example C-2 or C-4 but using in place of 3-amino-5-(4-methoxyphenyl)-2(1H)-pyridinone or 3-amino-5-(4-nitrophenyl)-2(1H)-pyridinone a molar equivalent quantity of the appropriate 3-amino-5-(methoxy- or nitrophenyl)-2(1H)-pyridinone, it is contemplated that the corresponding 3-amino-5-(hydroxy- or amino-phenyl)-2(1H)-pyridinones of Examples C-14 through C-19 can be obtained.

C-14. 3-Amino-5-(3-hydroxyphenyl)-2(1H)-pyridinone, using the procedure of Example C-2.

C-15. 3-Amino-5-(3,4-dihydroxyphenyl)-2(1H)-pyridinone, using the procedure of Example C-2.

C-16. 3-Amino-5-(4-methoxy-3-aminophenyl)-2-oxonicotinonitrile using the procedure of Example C-4.

C-17. 3-Amino-5-(3-aminophenyl)-2(1H)-pyridinone, using the procedure of Example C-4.

C-18. 3-Amino-5-(3,4-diaminophenyl)-2(1H)-pyridinone, using the procedure of Example C-4.

C-19. 3-Amino-5-(4-hydroxy-3-aminophenyl)-2(1H)-pyridinone, using the procedure of Example C-2.

Following the procedure described in Example C-1 but using in place of 1,2-dihydro-5-(4-methoxyphenyl)-2-oxonicotinamide a molar equivalent quantity of the appropriate 1,2-dihydro-5-(substituted-phenyl)-6-(loweralkyl)-2-oxonicotinamide, it is contemplated that the corresponding 3-amino-5-(substituted-phenyl)-6-(loweralkyl)-2(1H)-pyridinones of Examples C-20 to C-23 can be obtained.

C-20. 3-amino-5-(3-methoxyphenyl)-6-methyl-2(1H)-pyridinone, m.p. 243°–245° C.

C-21. 3-Amino-5-(3,4-dimethoxyphenyl)-6-methyl-2(1H)-pyridinone, m.p. 222°–224° C.

C-22. 3-Amino-5-(4-nitrophenyl)-6-methyl-2(1H)-pyridinone.

C-23. 3-Amino-5-(4-methoxyphenyl)-6-ethyl-2(1H)-pyridinone.

Following the procedure described in Example C-2 or C-4 but using in place of 3-amino-5-(4-methoxy- or 4-nitrophenyl)-2(1H)-pyridinone a molar equivalent quantity of the appropriate 3-amino-5-(methoxy- or nitrophenyl)-2(1H)-pyridinone, it is contemplated that the corresponding compounds of Examples C-24 through C-27 can be obtained.

C-24. 3-Amino-5-(3-hydroxyphenyl)-6-methyl-2(1H)-pyridinone, m.p. 251°–253° C.

C-25. 3-Amino-5-(3,4-dihydroxyphenyl)-6-methyl-2(1H)-pyridinone, m.p. 266° C. (chars.)

C-26. 3-Amino-5-(4-aminophenyl)-6-methyl-2(1H)-pyridinone.

C-27. 3-Amino-5-(4-hydroxyphenyl)-6-ethyl-2(1H)-pyridinone.

Following the procedure described in Example C-1 but using in place of 1,2-dihydro-5-(4-methoxyphenyl)-2-oxonicotinamide a molar equivalent quantity of the appropriate 1-$R_1$-1,2-dihydro-5-(substituted-phenyl)-6-R-2-oxonicotinamide, it is contemplated that the corresponding 3-amino-1-$R_1$-5-(substituted-phenyl)-6-R-2(1H)-pyridinones of Examples C-28 through C-31 can be obtained.

C-28. 3-Amino-5-(4-methoxyphenyl)-1,6-dimethyl-2(1H)-pyridinone.

C-29. 3-Amino-1-(2-hydroxyethyl)-5-(4-methoxyphenyl)-6-methyl-2(1H)-pyridinone.

C-30. 3-Amino-5-(4-hydroxyphenyl)-1,6-dimethyl-2(1H)-pyridinone.

C-31. 3-Amino-1-(2-hydroxyethyl)-5-(4-hydroxyphenyl)-6-methyl-2(1H)-pyridinone.

The usefulness of the compounds of formula I, II or III or salts thereof (those of I and certain basic compounds of II or III as identifed above) as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of formula I, II or III or pharmaceutically acceptable acid-addition salts thereof (those of I and certain basic compounds of II or III as identified above) at doses of 3, 10, 30, and/or 100 μg/ml., were found to cause significant increases, that is, greater than 25% (cat) or 30% (g.pig) in papillary muscle force and significant increases, that is, greater than 25% (cat) or 30% (g.pig) in right atrial force, while causing a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. The compounds of the invention have varying degrees of cardiotonic activity. For example, the particularly preferred embodiment of Example C-6 was found to cause guinea pig papillary muscle force and right atrial force increases of 110% and 109% at a dose level as low as 10 μg/ml. Other embodiments, e.g., Examples C-2, C-4 and C-8 had significant activity at 100 μg/ml in the cat atria and papillary muscle test procedure but not at said lower doses, i.e., at 10 and 30 μg/ml. Other illustrative cat or guinea pig papillary muscle and right atrial rate increases for compounds of the invention are: 73% and 82% at 10 μg/ml. for Example A-6 (g.pig); 33% and 33% at 30 μg/ml. and 70% and 37% at 100 μg/ml. for Example A-4 (cat); 67% and 25% at 10 μg/ml. for Example A-2 (cat); 133% and 71% at 10 μg/ml. for Example A-23 (g.pig); and, 121% and 72% at 10 μg/ml for Example A-26.

When tested by said anesthetized dog procedure, the compounds of formula I, II or III or pharmaceutically acceptable acid-addition salts thereof (those of I and said basic compounds of II or III) at doses of 1.0, 3.0 and/or 10 mg/kg. administered intravenously were found to cause significant increases, that is, 25% or greater, in cardiac contractile force or cardiac contractility with lower changes in heart rate and blood pressure. For example, when tested at one or more of said dose levels by this procedure, the compound of Example C-2 was found to cause increases of 34 to 156% in contractile force and lower changes in heart rate and blood pressure.

The present invention includes within its scope a cardiotonic composition for increasing cardiac contractility, said composition comprising a pharmaceutically acceptable carrier and, as the active component thereof, a cardiotonically effective amount of the compound of formula I, II or III or pharmaceutically acceptable acid-addition salt thereof (those of I and said basic compounds of II or III). The invention also includes within its scope the method for increasing cardiac contractility in a patient requiring such treatment which comprises administering to such patient said cardiotonic composition providing a cardiotonically effective amount of said compound of formula I, II or III or pharmaceutically acceptable acid-addition salt thereof (those of I and said basic compounds of II or III). In clinical practice said compound or salt thereof will normally be administered orally or parenterally in a wide variety of dosage forms.

Solid compositions for oral administration include compressed tablets, pills, powders and granules. In such solid compositions, at least one of the active compounds is amixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. In addition to inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement, using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. A 1-$R_1$-3-amino-5-(3-R'-4-R''-phenyl)-6-R-2(1H)-pyridinone having the formula

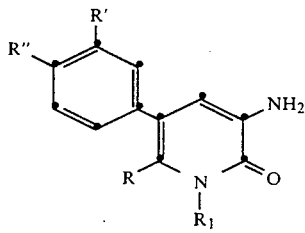

or acid-addition salt thereof, where $R_1$ is hydrogen, lower-alkyl or lower-hydroxyalkyl, R is lower-alkyl, and, R' and R'' are each hydrogen, amino or hydroxy at least one of R' or R'' being other than hydrogen.

2. A compound according to claim 1 where $R_1$ is hydrogen, R is methyl or ethyl, R' is hydrogen, hydroxy or amino and R'' is hydroxy or hydrogen the latter only when R' is other than hydrogen.

3. 3-Amino-5-(4-hydroxyphenyl)-6-methyl-2(1H)-pyridinone or pharmaceutically acceptable acid-addition salt thereof.

4. 3-Amino-5-(3,4-dihydroxyphenyl)-6-methyl-2(1H)-pyridinone or pharmaceutically acceptable acid-addition salt thereof.

5. A cardiac composition for increasing cardiac contractility, said composition comprising a pharmaceutically acceptable carrier and, as the active component thereof, a cardiotonically effective amount of 1-$R_1$-3-amino-5-(3-R'-4-R''-phenyl)-6-R-2(1H)-pyridinone or pharmaceutically acceptable acid-addition salt thereof, where $R_1$ is hydrogen, lower-alkyl or lower-hydroxyalkyl, R is lower-alkyl, and R' and R'' are each hydrogen, amino or hydroxy at least one of R' and R'' being other than hydrogen.

6. A composition according to claim 5 where $R_1$ is hydrogen, R is methyl or ethyl, R' is hydrogen, hydroxy or amino and R'' is hydroxy or hydrogen, the latter only when R' is other than hydrogen.

7. A composition according to claim 6 where the active component is 3-amino-5-(4-hydroxyphenyl)-6-methyl-2(1H)-pyridinone or pharmaceutically acceptable, acid-addition salt thereof.

8. The method for increasing cardiac contractility in a patient requiring such treatment which comprises administering orally or parenterally in a solid or liquid dosage form to such patient a composition comprising a pharmaceutically acceptable carrier and, as active component thereof, a cardiotonically effective amount of 1-$R_1$-3-amino-5-(3-R'-4-R''-phenyl)-6-R-2(1H)-pyridinone or pharmaceutically-acceptable salt thereof, where $R_1$ is hydrogen, lower-alkyl or lower-hydroxyalkyl, R is hydrogen or lower-alkyl, R' and R'' are each hydrogen, amino or hydroxy at least one of R' and R'' being other than hydrogen.

9. The method according to claim 8 where $R_1$ is hydrogen, R is methyl or ethyl, R' is hydrogen, hydroxy or amino and R'' is hydroxy or hydrogen the latter only when R' is other that hydrogen.

10. The method according to claim 9 where the active component is 3-amino-5-(4-hydroxyphenyl)-6-methyl-2(1H)-pyridinone or pharmaceutically acceptable acid addition salt thereof.

11. A 1-$R_1$-3-amino-5-(3-R'-4-R''-phenyl)-6-R-2(1H)-pyridinone having the formula

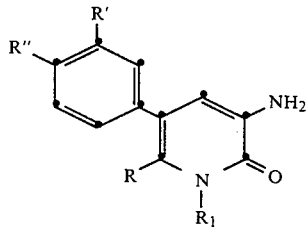

or acid-addition salt thereof, where $R_1$ is hydrogen, lower-alkyl or lower-hydroxyalkyl, R is lower-alkyl, and, R' and R'' are each hydrogen or methoxy at least one of R' or R'' being methoxy.

12. A compound according to claim 11 where $R_1$ is hydrogen, R is methyl or ethyl, R' is hydrogen or methoxy and R'' is methoxy or hydrogen, the latter only when R' is methoxy.

13. 3-Amino-5-(4-methoxyphenyl)-6-methyl-2(1H)-pyridinone or acid-addition salt thereof.

* * * * *